US007909806B2

(12) United States Patent  
Goodman et al.

(10) Patent No.: US 7,909,806 B2
(45) Date of Patent: *Mar. 22, 2011

(54) CORD BLOOD AND PLACENTA COLLECTION KIT

(75) Inventors: Chris B. Goodman, Green Brook, NJ (US); Debra Kapnick, Randolph, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 423 days.

This patent is subject to a terminal disclaimer.

(21) Appl. No.: 11/999,608

(22) Filed: Dec. 5, 2007

(65) Prior Publication Data

US 2008/0208158 A1 Aug. 28, 2008

Related U.S. Application Data

(60) Continuation-in-part of application No. 11/589,018, filed on Oct. 27, 2006, now abandoned, which is a division of application No. 11/230,760, filed on Sep. 20, 2005, now Pat. No. 7,147,626.

(60) Provisional application No. 60/612,408, filed on Sep. 23, 2004.

(51) Int. Cl.
  *A61M 1/00* (2006.01)
  *A61B 19/00* (2006.01)
  *A01N 1/02* (2006.01)
  *A61B 17/32* (2006.01)

(52) U.S. Cl. ........ 604/317; 604/408; 604/409; 604/410; 435/1.1; 435/2; 435/307.1; 606/119; 606/120

(58) Field of Classification Search .................. 604/40, 604/317; 606/119, 120; 435/2, 1.1, 372, 435/261.4, 307.1; 424/529, 93.1, 93.7
See application file for complete search history.

(56) References Cited

U.S. PATENT DOCUMENTS

| 5,004,681 | A |   | 4/1991 | Boyse et al. ................. 436/2 |
| 5,192,553 | A |   | 3/1993 | Boyse et al. ................. 424/529 |
| 5,372,581 | A |   | 12/1994 | Anderson ..................... 604/32 |
| 5,415,665 | A |   | 5/1995 | Hessel et al. ................. 606/120 |
| 5,919,176 | A | * | 7/1999 | Kuypers et al. .............. 604/317 |
| 5,993,429 | A | * | 11/1999 | Kuypers et al. .............. 604/317 |
| 6,238,907 | B1 | * | 5/2001 | Schuler-Maloney et al. .................... 435/284.1 |
| 7,147,626 | B2 | * | 12/2006 | Goodman et al. ............. 604/317 |
| 2003/0064503 | A1 | * | 4/2003 | Abuljadayel ............... 435/285.1 |
| 2004/0048372 | A1 |   | 3/2004 | Hariri |
| 2005/0233298 | A1 | * | 10/2005 | Farsedakis .................. 435/1.1 |

OTHER PUBLICATIONS

Cold Chain Technologies, Design and Testing Services, online @ www.coldchaintech.com, Jun. 9, 2006.
Cold Chain Technologies, Engineered Solutions for Thermal Packaging, online @ www.coldchaintech.com, Jun. 9, 2006.
Cold Chain Technologies, Koolit Refrigerants, online @ www.coldchaintech.com, Jun. 9, 2006.

(Continued)

Primary Examiner — Jacqueline F. Stephens
(74) Attorney, Agent, or Firm — Jones Day

(57) ABSTRACT

The present invention provides an improved kit for the collection of umbilical cord blood and placental blood, and collection of the placenta from which such blood is obtained. The kit improves upon existing kits in that it provides for improved user convenience, provides for the collection of the placenta itself, and better maintains the internal temperature of the container in which the collected blood and placenta are shipped to a blood bank or registry. The invention further provides a method of collecting umbilical cord and placental blood, and the placenta from which such blood is obtained, comprising using the kit described herein.

22 Claims, 2 Drawing Sheets

OTHER PUBLICATIONS

Figure 1:
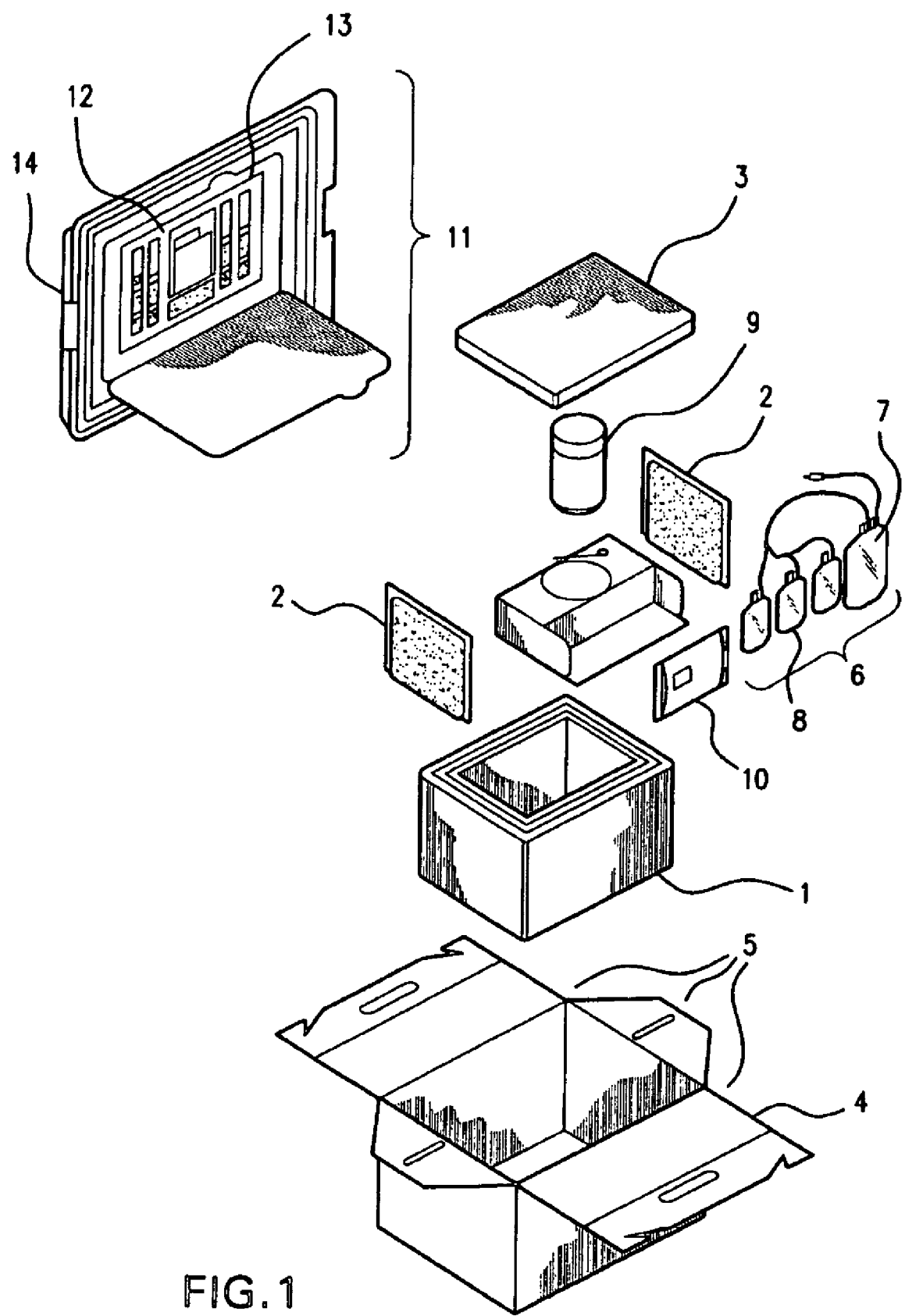

Cold Chain Technologies, Koolit Foam Bricks, online @ www.coldchaintech.com, Jun. 9, 2006.
Cold Chain Technologies, Koolit Gel Packs, online @ www.coldchaintech.com, Jun. 9, 2006.
Cold Chain Technologies, Koolit Gel Bottles, online @ www.coldchaintech.com, Jun. 9, 2006.
Cold Chain Technologies, Insulated Containers, online @ www.coldchaintech.com, Jun. 9, 2006.
Product: STP-101, Refurbishment kit for the STP-100, online Order Catalogue, SaftSupply @ www/saf-t-supply.com/shopper_catalog, Jun. 9, 2006.
Product: STP-101a, Refurbishment box for the STP-100, online Order Catalogue, SaftSupply @ www/saf-t-supply.com/shopper_catalog, Jun. 9, 2006.
Product: STP-102, Bubble wrap and sorbent, online Order Catalogue, SaftSupply @ www/saf-t-supply.com/shopper_catalog, Jun. 9, 2006.
Product: STP-104, Secondary container, online Order Catalogue, SaftSupply @ www/saf-t-supply.com/shopper_catalog, Jun. 9, 2006.
Product: STP-105, Replacement Orings, online Order Catalogue, SaftSupply @ www/saf-t-supply.com/shopper_catalog, Jun. 9, 2006.
Product: STP-106, foam insert, online Order Catalogue, SaftSupply @ www/saf-t-supply.com/shopper_catalog, Jun. 9, 2006.
Product: STP-111, Refurbishment inner box for the STP-100, STP-310, STP-320, online Order Catalogue, SaftSupply @ www/saf-t-supply.com/shopper_catalog, Jun. 9, 2006.
Product: STP-150, 50 ml Absorbent strip, online Order Catalogue, SaftSupply @ www/saf-t-supply.com/shopper_catalog, Jun. 9, 2006.
Product: STP-151, 100 ml Absorbent strip, online Order Catalogue, SaftSupply @ www/saf-t-supply.com/shopper_catalog, Jun. 9, 2006.
Product: STP-301, Refurbishment for the STP-300 insulated overpack, online Order Catalogue, SaftSupply @ www/saf-t-supply.com/shopper_catalog, Jun. 9, 2006.
Product: STP-303, Mailing flap for the STP-300, STP-310, STP-320, online Order Catalogue, SaftSupply @ www/saf-t-supply.com/shopper_catalog, Jun. 9, 2006.
Product: STP-3081, Replacement box for the STP-308 Medium cooler, online Order Catalogue, SaftSupply @ www/saf-t-supply.com/shopper_catalog, Jun. 9, 2006.
Product: STP-3091, Replacement box for the STP-308 Small cooler, online Order Catalogue, SaftSupply @ vvww/saf-t-supply.com/shopper_catalog, Jun. 9, 2006.
Product: STP-311, Refurbishment kit for the STP-310, online Order Catalogue, SaftSupply @ www/saf-t-supply.com/shopper_catalog, Jun. 9, 2006.
Product: STP-312, Upgrade kit for the STP-300, online Order Catalogue, SaftSupply @ www/saf-t-supply.com/shopper_catalog, Jun. 9, 2006.
Product: STP-314, –10C Freezer Packs, online Order Catalogue, SaftSupply @ www/saf-t-supply.com/shopper_catalog, Jun. 9, 2006.
Product: STP-315, 20-24C Bricks, online Order Catalogue, SaftSupply @ www/saf-t-supply.com/shopper_catalog, Jun. 9, 2006.
Product: STP-316, 10-25 Bricks, online Order Catalogue, SaftSupply @ www/saf-t-supply.com/shopper_catalog, Jun. 9, 2006.
Product: STP-316A, 10-25C Refrigerant Bricks, online Order Catalogue, SaftSupply @ www/saf-t-supply.com/shopper_catalog, Jun. 9, 2006.
Product: STP-316B, 10-25 PCM Bricks, online Order Catalogue, SaftSupply @ vvvvw/saf-t-supply.com/shopper_catalog, Jun. 9, 2006.
Product: STP-317, 15-30C Bricks, online Order Catalogue, SaftSupply @ www/saf-t-supply.com/shopper_catalog, Jun. 9, 2006.
Product: STP-319, 2-8C REfrigerant Bricks—new configuration, online Order Catalogue, SaftSupply @ www/saf-t-supply.com/shopper_catalog, Jun. 9, 2006.
Product: STP-321, Outer box for STP 320, online Order Catalogue, SaftSupply @ vvww/saf-t-supply.com/shopper_catalog, Jun. 9, 2006.
Product: STP-351, Refurbishment kit for STP-350 Infectious substance shipper, online Order Catalogue, SaftSupply @ www/saf-t-supply.com/shopper_catalog, Jun. 9, 2006.
Product: STP-610, Saf-T-Rap—Sticky bubble wrap, online Order Catalogue, SaftSupply @ www/saf-t-supply.com/shopper_catalog, Jun. 9, 2006.
Product: STP-700, Patented Saf-T-Pak+ Secondary Container, online Order Catalogue, SaftSupply @ www/saf-t-supply.com/shopper_catalog, Jun. 9, 2006.
Product: STP-710, Patented Saf-T-Pak+ Secondary Container, online Order Catalogue, SaftSupply @ www/saf-t-supply.com/shopper_catalog, Jun. 9, 2006.
Product: STP-711 Inner bag only, online Order Catalogue, SaftSupply @ www/saf-t-supply.com/shopper_catalog, Jun. 9, 2006.
Product: STP-714 Tuck and Fold Secondary Pressure Vessel, online Order Catalogue, SaftSupply @ www/saf-t-supply.com/shopper_catalog, Jun. 9, 2006.
Product: STP-352, Secondary Container kit for STP-350 Infectious substance shipper, online Order Catalogue, SaftSupply @ www/saf-t-supply.com/shopper_catalog, Jun. 9, 2006.
Product: STP-371, Refurbishment for STP-370 Insulated Infectious subatnce shipper, online Order Catalogue, SaftSupply @ www/saf-t-supply.com/shopper_catalog, Jun. 9, 2006.
Product: STP-410—0 C Bricks, online Order Catalogue, SaftSupply @ www/saf-t-supply.corn/shopper_catalog, Jun. 9, 2006.
Product: STP-600 Saf-T-Pouch holds 5×10 ml tubes, online Order Catalogue, SaftSupply @ www/saf-t-supply.com/shopper_catalog, Jun. 9, 2006.
Product: STP-609 Saf-T-Pak Bubble Wrap—Small, online Order Catalogue, SaftSupply @ www/saf-t-supply.com/shopper_catalog, Jun. 9, 2006.
Product: STP-370 Patented Saf-T-Pak+ Secondary Container, online Order Catalogue, SaftSupply @ www/saf-t-supply.com/shopper_catalog, Jun. 9, 2006.
Product: STP-740 Patented Saf-T-Pak+ Secondary Container, online Order Catalogue, SaftSupply @ www/saf-t-supply.com/shopper_catalog, Jun. 9, 2006.
Product: STP-741 Inner bag only, online Order Catalogue, SaftSupply @ wvvw/saf-t-supply.com/shopper_catalog, Jun. 9, 2006.
Product: STP-800, Shipper's Declaration of Dangerous Goods, online Order Catalogue, SaftSupply @ www/saf-t-supply.com/shopper_catalog, Jun. 9, 2006.
Product: STP-801, Shipper's Declaration of Dangerous Goods Bulk Pak, online Order Catalogue, SaftSupply @ www/saf-t-supply.com/shopper_catalog, Jun. 9, 2006.
Product: STP-802, IInfectious substance lebels, online Order Catalogue, SaftSupply @ www/saf-t-supply.com/shopper_catalog, Jun. 9, 2006.
Product: STP-803, Miscellaneous Hazard labels, online Order Catalogue, SaftSupply @ www/saf-t-supply.com/shopper_catalog, Jun. 9, 2006.
Product: STP-804, Dry Ice Quantity labels, online Order Catalogue, SaftSupply @ www/saf-t-supply.com/shopper_catalog, Jun. 9, 2006.
Product: STP-806, Cargo Aircraft Only labels, online Order Catalogue, SaftSupply @ www/saf-t-supply.com/shopper_catalog, Jun. 9, 2006.
Product: STP-807, Shipper asddress labels, online Order Catalogue, SaftSupply @ www/saf-t-supply.com/shopper_catalog, Jun. 9, 2006.
Product: STP-808, Consignee address lanels, online Order Catalogue, SaftSupply @ www/saf-t-supply.com/shopper_catalog, Jun. 9, 2006.
Product: STP-809 Special Saf-T-Pak Triangular UN 2814 labels, online Order Catalogue, SaftSupply @ www/saf-t-supply.com/shopper_catalog, Jun. 9, 2006.
Product: STP-809, blockout labels, online Order Catalogue, SaftSupply @ www/saf-t-supply.com/shopper_catalog, Jun. 9, 2006.

Product: STP-812, Shipper's Declaration of Dangerous Goods—ambient shipment, online Order Catalogue, SaftSupply @ www/saf-t-supply.com/shopper_catalog, Jun. 9, 2006.
Product: STP-813, Blank shipper's Declaration forms (candy stripe), online Order Catalogue, SaftSupply @ www/saf-t-supply.com/shopper_catalog, Jun. 9, 2006.
Product: STP-816 Special Saf-T-Pak Triangular UN 2900 labels, online Order Catalogue, SaftSupply @ www/saf-t-supply.com/shopper_catalog, Jun. 9, 2006.
Product: STP-817, overpack labels, online Order Catalogue, SaftSupply @ www/saf-t-supply.com/shopper_catalog, Jun. 9, 2006.
Product: STP-818, Diamond Shaped UN 3373 labels, online Order Catalogue, SaftSupply @ www/saf-t-supply.com/shopper_catalog, Jun. 9, 2006.

* cited by examiner

CORD BLOOD AND PLACENTA COLLECTION KIT

This application is a continuation-in-part of, and claims priority to, U.S. patent application Ser. No. 11/589,018, filed Oct. 27, 2006, now abandoned which is a divisional of U.S. patent application Ser. No. 11/230,760, filed Sep. 20, 2005, now U.S. Pat. No. 7,147,626 and claims the benefit of U.S. Provisional Application No. 60/612,408, filed Sep. 23, 2004, each of which is hereby incorporated herein in its entirety.

1. FIELD OF THE INVENTION

The present invention relates to kits for the collection of a placenta, and of placental blood and umbilical cord blood, at the time of birth. The kits provide improved user convenience features, and optionally improved temperature stabilization during shipping, compared to existing collection kits.

2. BACKGROUND OF THE INVENTION

2.1 Stem Cells and Cord Blood

There is considerable interest in the identification, isolation and generation of human stem cells. Human stem cells are totipotential or pluripotential precursor cells capable of generating a variety of mature human cell lineages. This ability serves as the basis for the cellular differentiation and specialization necessary for organ and tissue development.

Recent success at transplanting such stem cells have provided new clinical tools to reconstitute and/or supplement bone marrow after myeloablation due to disease, exposure to toxic chemical and/or radiation. Further evidence exists that demonstrates that stem cells can be employed to repopulate many, if not all, tissues and restore physiologic and anatomic functionality. The application of stem cells in tissue engineering, gene therapy delivery and cell therapeutics is also advancing rapidly.

Many different types of mammalian stem cells have been characterized. For example, embryonic stem cells, embryonic germ cells, adult stem cells or other committed stem cells or progenitor cells are known. Certain stem cells have not only been isolated and characterized but have also been cultured under conditions to allow differentiation to a limited extent. A basic problem remains, however, in that obtaining sufficient quantities and populations of human stem cells which are capable of differentiating into many cell types is near impossible. Stem cells are in critically short supply. These are important for the treatment of a wide variety of disorders, including malignancies, inborn errors of metabolism, hemoglobinopathies, and immunodeficiencies.

Umbilical cord blood ("cord blood") is a source of hematopoietic progenitor stem cells. Stem cells from cord blood are routinely cryopreserved for use in hematopoietic reconstitution, a widely used therapeutic procedure used in bone marrow and other related transplantations (see e.g., Boyse et al., U.S. Pat. No. 5,004,681; Boyse et al., U.S. Pat. No. 5,192,553). Conventional techniques for the collection of cord blood are based on the use of a needle or cannula, which is used with the aid of gravity to drain cord blood from (i.e., exsanguinate) the placenta (Boyse et al., U.S. Pat. No. 5,192,553; Boyse et al., U.S. Pat. No. 5,004,681; Anderson, U.S. Pat. No. 5,372,581; Hessel et al., U.S. Pat. No. 5,415,665). The needle or cannula is usually placed in the umbilical vein and the placenta is gently massaged to aid in draining cord blood from the placenta. In addition to cord blood, the placenta is now known to be a source of useful stem and progenitor cells. See, e.g., Hariri, United States Application Publication No. 2004/0048372 A1.

2.2 Umbilical Cord and Placental Blood Collection

The collection of blood at birth from the umbilical cord and placenta is an increasingly popular choice for parents, and an expanding business for cord blood and stem cell banks and registries. Typically, such banks and registries contract with prospective parents for stem cell and/or umbilical cord blood banking services. As part of the service, a bank or registry will send clients a collection kit for use at the time of delivery.

Current kits, however, typically do not provide shipping containers that prevent substantial temperature fluctuations during shipping. The kit provided by New England Cord Blood Bank, Inc., for example, provides a thin, uninsulated cardboard container for shipping the collected blood. However, it is important to maintain the internal temperature of the kit during shipping, as cord blood cells, particularly stem cells, do not tolerate sharp or sustained deviations from a temperature range from room temperature to body temperature. Temperature maintenance is important, too, because stem cells obtainable from cord blood and the placenta are finite in number, and in general, the more that may be delivered to a recipient in a medical procedure, the greater the chance of success.

Another limitation of current kits is that they do not provide for the collection and transport of the placenta. This is a significant limitation, as the placenta is now known to contain large numbers of embryonic-like stem cells and hematopoietic progenitor cells, which may be used in the same manner as stem and progenitor cells collected from cord blood. See Hariri, United States Application Publication No. 2004/0048372 A1. Thus, preservation of the placenta is as important as preservation of cord blood.

The cord blood and placenta collection kit of the present invention improves upon existing kits in several ways. First, it provides a significantly more stable interior temperature under shipping conditions than do existing kits. Second, it provides for the collection and shipping of the placenta. Finally, the contents of the kit are arranged so as to substantially increase the kit's user-friendliness.

3. SUMMARY OF THE INVENTION

The present invention provides a kit for the collection of placental and umbilical cord blood, and of a placenta, comprising (a) a container for the collection of said blood; (b) a container for the collection of said placenta; (c) materials sufficient for the collection of maternal blood; (d) instructions, wherein said instructions comprise a first set of instructions for the collection of maternal blood and a second set of instructions for the collection of umbilical cord and placental blood, wherein said first and second set of instructions are differently coded; and (e) an insulating container of sufficient capacity to contain items (a)-(d) prior to use, and items (a)-(c) after said collection of placental and umbilical cord blood, and of said placenta.

In another specific embodiment of the kit, said container for the collection of blood is a blood bag. In a more specific embodiment, the blood bag is a single or individual blood bag; the kit can comprise a plurality of single or individual bags. In a more specific embodiment, said blood bag comprises a collection bag and three satellite bags that are each smaller than said collection bag. In a specific embodiment of the cord blood collection bag, the bag comprises an anticoagulant. In a more specific embodiment, the anticoagulant is citrate-phosphate-dextrose (CPD). In another specific embodiment, the cord blood collection bag is sterile for collection associated with Caesarian section delivery.

In another specific embodiment, said materials for the collection of maternal blood comprises a plurality of vials and one or more needles suitable for the collection of blood. The needles can be any needles suitable for the collection of blood, but are preferably from 20 gauge to 24 gauge, e.g., 21 or 22 gauge. In more specific embodiment, at least one of said plurality of vials comprises EDTA, and at least one of said plurality of vials does not contain EDTA. In another more specific embodiment, said materials for the collection of maternal blood are contained within a first container separate from the remaining contents of the kit. In an even more specific embodiment, said first container fits into a cavity in the lid of said insulating container. In another more specific embodiment, the materials for the collection of maternal blood are contained within an insert, e.g., a foam insert, in the insulating container. In another more specific embodiment, said materials for the collection of maternal blood comprise two vials containing EDTA and two vials not containing EDTA. In another more specific embodiment, said first container additionally comprises color-coded instructions for the use of said materials for the collection of maternal blood.

In another specific embodiment of the kit, the insulating container comprises a box, wherein said box comprises a cardboard exterior and an insulating lining around the interior of said box. In a more specific embodiment, said insulating lining is STYROFOAM™. In another more specific embodiment, said insulating lining is about 0.5 inches to about 1.0 inches in thickness. In an even more specific embodiment, said lining is about 0.75 inches in thickness. In another specific embodiment of the kit, said insulating container has a R value of between about 5 and about 8. In a more specific embodiment, said insulating container has an R value of about 6.5. In another more specific embodiment, the internal volume of said insulating container is between 4 and 8 liters. In a more specific embodiment, the volume of said insulating container is about 6 liters. In another more specific embodiment, said insulating container comprises a lid having a central cavity suitable for receiving a first container that comprises a plurality of kit contents.

Figure 2:
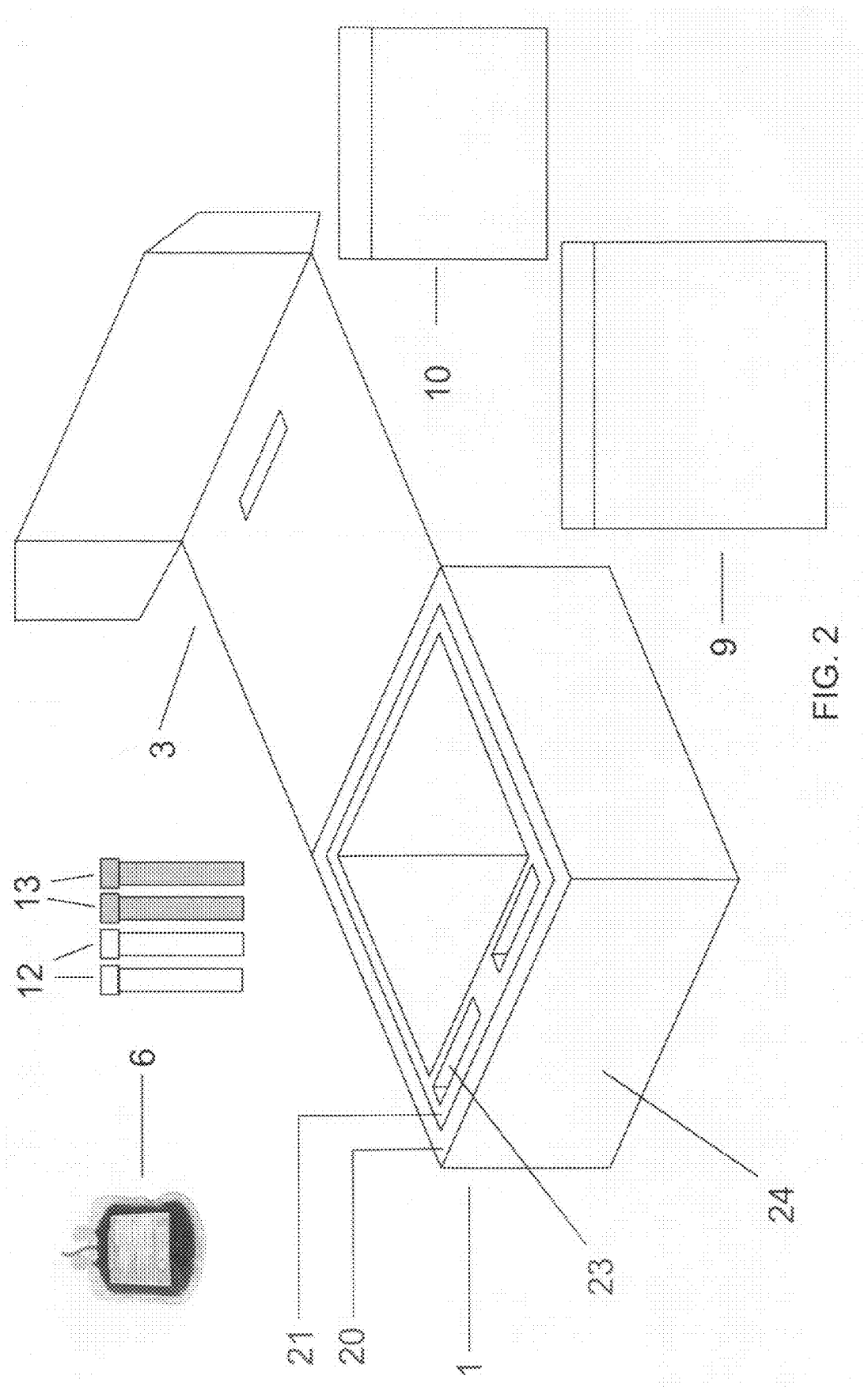

In another embodiment, the insulating container is an attaché-style carrying case or box, e.g., a carrying case or box comprising a handle, e.g., a plastic handle, that enables the user to carry the kit as an attaché case or briefcase is carried (see, e.g., 24 in FIG. 2).

In another specific embodiment, said insulating container comprises an insert. In a more specific embodiment, the insert comprises one or more spaces capable of holding said materials for the collection of maternal blood, container for the collection of umbilical cord blood, and container for the collection of said placenta. In a more specific embodiment, said insert is a foam insert. In a more specific embodiment, said insert comprises a first space to hold said container for the collection of said blood and a container for the collection of said placenta and a second space to hold said materials sufficient for the collection of maternal blood. In an even more specific embodiment, said insert comprises a first space to hold said container for the collection of said blood and a container for the collection of said placenta, a second space to hold maternal blood draw tubes, and a third space to hold other materials for collection of maternal blood, e.g., one or more needles. In another more specific embodiment, said insert fits snugly against the interior of the insulating container.

In a specific embodiment, the kit optionally comprises a temperature controlling composition. In another specific embodiment, said temperature controlling composition is a temperature controlling composition that resists temperature spikes. In another embodiment of the kit, said temperature controlling composition is a temperature controlling composition that resists temperature drops. In another embodiment, said refrigerant is a temperature controlling composition that resists both temperature spikes and temperature drops. In various specific embodiments, the invention provides any of the kits above wherein said temperature controlling composition is in brick or pack form. In another embodiment, said kit comprises a plurality of temperature controlling composition bricks or refrigerant packs. In a specific embodiment, said kit contains two temperature controlling composition packs. In a more specific embodiment, said kit is designed to contain at least two temperature controlling composition packs in a vertical configuration on opposite sides of the interior of said insulating container. In another specific embodiment, the kit comprises two temperature controlling composition packs, wherein at least one of said instructions instructs the user to place at least one pack under said umbilical cord blood and said placenta, and at least one pack on top of said umbilical cord blood and said placenta, prior to shipping. In another specific embodiment, the kit comprises a sufficient volume of temperature controlling composition to maintain the interior of said insulating container between 15° C. and 37° C. during shipping of said kit to a cord blood bank or cord blood registry. In a more specific embodiment, the kit comprises a sufficient volume of temperature controlling composition to maintain the interior of said insulating container between 15° C. and 37° C. during at least 12 hours of shipping of said kit to a cord blood bank or cord blood registry. In another more specific embodiment, said temperature controlling composition comprises a plurality of Saf-T-Pak STP-317 15-30C refrigerant bricks or their equivalent.

The invention further provides a method for the collection of umbilical cord blood and placental blood, and of a placenta, comprising using a kit which comprises (a) a container for the collection of said blood; (b) a container for the collection of said placenta; (c) materials sufficient for the collection of maternal blood; (d) instructions, wherein said instructions comprise a first set of instructions for the collection of maternal blood and a second set of instructions for the collection of umbilical cord and placental blood, wherein said first and second set of instructions are differently coded; and (e) an insulating container of sufficient capacity to contain items (a)-(d) prior to use, and items (a)-(c) after said collection of placental and umbilical cord blood, and of said placenta. In a specific embodiment, the kit used in the method further comprises a temperature controlling composition, typically provided in the form of, e.g., pouches or bricks comprising the composition.

The invention also provides one or more bags for the collection of umbilical cord and placental blood. The blood bag can be a single (individual) bag(s). In another specific embodiment, the blood bag has the capacity to contain about 100 mL to about 1000 mL of blood, e.g., about 250 mL of blood. In a specific embodiment, the blood bag comprises a collection bag and a plurality of satellite bags, each of which is smaller in volume than said collection bag. In a specific embodiment, said collection bag has the capacity to hold about 250 ml of blood. In another specific embodiment, said satellite bags is joined to said collection bag by plastic tubing.

4. BRIEF DESCRIPTION OF THE DRAWINGS

FIG. 1 depicts one embodiment of the cord blood and placenta collection kit described herein. 1: insulating container; 2: temperature controlling composition; 3: lid; 4: box, e.g., for shipping kit; 5: flaps on box; 6: blood bag, embodied as a blood bag comprising a collection bag 7 and three smaller satellite bags 8; 9: container (canister) for storing collected placenta; 10: plastic bag into which placenta may be placed prior to placement in container 9; 11: kit for collection of maternal blood; 12: vials containing EDTA; 13: vials not containing EDTA; 14: plastic tray containing maternal blood collection components.

FIG. 2 depicts another embodiment of the cord blood and placenta collection kit described herein. 1: insulating container; 3: lid; 6: blood bag, embodied as a single or individual blood bag; 9: container (plastic bag, e.g., rated to withstand 95 kPa distributed internal pressure) for storing collected placenta; 10: plastic bag into which placenta may be placed prior to placement in container 9; 12: vials containing EDTA; 13: vials not containing EDTA; 20: insulating material (e.g., Styrofoam); 21: foam insert; 23: spaces in foam insert for storage of kit components; 24: handle (attaché-style carrying case or box).

5. DETAILED DESCRIPTION OF THE INVENTION

The present invention provides improved kits for the collection of placental and umbilical cord blood, and of the placenta, at the time of birth. The kits provide for increased convenience for the user, and for improved maintenance and stability of the collected material during shipping. The kits comprise all of the materials necessary for cord blood and placental collection at the time of delivery, and containers for shipping the collected blood and placenta to a cord blood and/or stem cell bank.

It has been discovered that a cord blood and placenta collection kit, configured, for example, as shown in FIG. 2, does not require the use of a separate temperature-controlling composition, and that shipment of the collected materials in the insulating container is sufficient to maintain collected cord blood and placenta, including cord blood and placental stem cells, in a viable state during shipping, e.g., during shipping for about, or for up to about, 12, 18, 24, 30, 36, 42, 48, 54, 60, 66 or 72 hours.

In one embodiment, shown in FIG. 2, insulating container 1 comprises a box having an interior surface, wherein the interior surface optionally comprises a layer of an insulating material 20. The box can be made of, e.g., corrugated cardboard or a similar material suitable for shipping. In a more specific embodiment, substantially all of the interior surface of the box is covered with said insulating material. In another more specific embodiment, the insulating material is STYROFOAM™. In this embodiment, the insulating container, including cardboard box and insulating material, is designed for shipment of the collected materials to be processed. The insulating container optionally comprises a foam insert 21, which, in combination with the insulating container and under standard shipping and use conditions, maintains the contents of the kit within a range of about 15° C. to about 30° C. over the course of about 24-72 hours, e.g., about 48 hours post-collection. In a specific embodiment, foam insert 21 advantageously comprises spaces 23 for storage of kit components. In one embodiment, foam insert 21, as depicted in FIG. 2, comprises three spaces for receiving and storing collection components, including collection components comprising collected materials such as cord blood and placenta; a large space holds the umbilical cord blood and placenta collection materials, while two smaller spaces hold the maternal blood-draw tubes and remaining maternal blood-draw materials, respectively.

In a specific embodiment in which the insulating container does not require a separate box for shipping, the kit also optionally comprises a second box 4 (FIG. 1) that contains the insulating container. Such a box improves handling and carriage of the kit by a user prior to shipping. In one embodiment, the second box is form-fitting over the insulating container, and is made of corrugated cardboard or similar material. In one embodiment, the top flaps 5 (FIG. 1) of the second box are shaped so as to make a carrying handle. For example, a first pair of opposite flaps are each longer than half the width of the second box, and have corresponding cutouts at the distal end, in one embodiment located in the center of the distal end, suitable for receiving a hand. Additionally, the first pair of opposing flaps has cutouts on the corners to create a flange at each corner. Further, in this example, the second pair of opposing flaps comprises a slit suitable for receiving, and locking to, the flanges on the first pair of opposing flaps, when the first pair of opposing flaps are brought together, thus forming a handle made from the first pair of opposing flaps, locked together by the second pair of opposing flaps. See, e.g., FIG. 1. In one embodiment, the second box is suitable for labeling and shipping by any overnight or next-day shipping service.

In another embodiment, the kit comprises an insulating container 1 and temperature controlling composition 2 (shown in one example configuration) that, under standard shipping and use conditions, maintains the contents of the kit within a range of about 15° C. to about 30° C. over the course of about 24-72 hours, e.g., about 48 hours post-collection. In one embodiment, the insulating container is a plastic insulating container. In a more specific embodiment, the insulating container is a STYROFOAM™ box. In this embodiment, the insulating container requires no other container, e.g., a box, e.g., a cardboard box, for shipping of the collected materials to be processed. In a specific embodiment, such a kit also comprises a temperature controlling composition (see below).

The insulating container may have an R-value (an indicator of insulating ability) of from about 2 to about 10; in certain embodiments, the R-value is between about 5 and about 8; in other embodiments, the R value is about 6.5. In determining an acceptable R value, both the value of temperature maintenance and the increased cost of shipping a thicker insulating container can be considered; an R value of approximately 6.5+/−1 acceptably insulates the kit contents and keeps shipping costs reasonable. The insulating container can be any size; in certain embodiments, the interior of the insulating container is just large enough to contain the kit contents. In various embodiments, the interior of the insulating container may be between about 2 to about 15 liters, between about 6 to about 13 liters, or, in some embodiments, approximately 11.5 liters.

The lid 3 of the insulating container may be a simple (i.e., unmodified) lid that fits atop the main portion of the insulating container. The lid may be completely separable from the main portion of the insulating container, or may be permanently affixed (e.g., hinged) thereto. In some embodiments, the lid has a first, central raised portion that snugly fits partway into the interior of the insulating container, such that part of the lid fits into the insulating container, and part rests on the upper lip of the insulating container. In one embodiment, the lid additionally comprises a second raised portion or lip, separate from and peripheral to the first raised portion, and the top lip of the insulating container comprises a channel into which the second raised portion of the lid fits snugly. In this embodiment, when the lid is placed onto the insulating container, the lip and channel engage, providing additional protection against leakage of the kit contents. In another more specific embodiment, the lid comprises a cavity in the first raised portion, which is capable of receiving and storing one or more of the kit contents. In one embodiment, the cavity contains kit components for a particular step in the collection process. In another embodiment, said kit components for a particular step are the kit components for maternal blood collection. In another embodiment, said maternal blood collection components are contained within a plastic tray that fits snugly into said cavity.

In an embodiment of the kit in which the insulating container comprises a box, e.g., a cardboard box, comprising an insulating material, and a foam insert (e.g., insert 21 as depicted in FIG. 2), materials for collection of maternal blood, umbilical cord and/or placenta can be carried or placed in the insert rather than in the lid. In this embodiment, the lid can comprise a layer of the insulating material such that, when the container is closed, the contents are substantially completely surrounded by the insulating material.

The kits of the invention further comprise components for collecting cord blood and placental blood. A typical blood collection from the umbilical cord and placenta nets 200-300 milliliters of blood; thus, the collection component is, in one embodiment, large enough to collect 200-300 milliliters of blood. In another embodiment, the collection component is large enough to collect all of the blood from a placenta and/or umbilical cord. In one embodiment, the collection component is a blood bag (e.g., exemplified by the multiple bag 6, shown in FIG. 1, or the single bag 6 shown in FIG. 2); however, a syringe may also be used.

In one embodiment, the blood bag is a single bag. The blood bag can be a standard blood bag, or a blood bag comprising a conical top that facilitates collection of cord blood. In a specific embodiment, the blood bag is configured with a main chamber and a plurality of smaller chambers (exemplified as 7 and 8, respectively, in FIG. 1), each joined to the main chamber such that fluid may flow from one chamber to the other. For example, the bags may be physically attached to each other such that the contents may flow directly from one to another, or they may be physically separate, joined only by tubing (e.g., TYGON™). In a specific embodiment, the blood bag comprises a main chamber of approximately 250 mL in volume, and three smaller chambers of approximately 50 mL in volume each, attached to the main chamber by plastic tubing.

In one embodiment, the blood bag contains an anticoagulant. Any medically-acceptable anticoagulant, such as heparin, may be used in the blood bag. In a specific embodiment, the anticoagulant is citrate-phosphate-dextrose (CPD). In another specific embodiment, the cord blood collection bag is sterile for collection associated with Caesarian section delivery.

The kits can also comprise a needle and tubing to connect the needle to the blood bag(s) during collection. The kit can also comprise a device, such as a tube clamp or slide clamp, e.g., for stripping the cord blood collection tubing or for maintenance of a closed tube/bag system after collection is complete.

The kits can also comprise one or more solutions or compositions for the sterilization of an area of the body, placenta or umbilical cord involved in the process of collection of cord blood, placenta, or maternal blood. In a specific embodiment, the solution or composition is a disinfectant. In a more specific embodiment, the disinfectant can comprise alcohol. In a more specific embodiment, the composition comprises isopropyl alcohol 70% (v/v) and chlorhexidine gluconate 2% (w/v). Examples of a solution or composition for sterilization include the CHLORAPREP® ONE-STEP FREPP® applicator, which delivers a solution of isopropyl alcohol 70% (v/v) and chlorhexidine gluconate 2% (w/v).

The kits also comprise a component 9 used for collecting and storing the placenta after removal of the placental blood. In one embodiment, the component is a flexible container, e.g., a plastic shipping bag. In a specific embodiment, the plastic shipping bag is able to, or is rated as being able to, withstand 95 kPa of distributed internal pressure, e.g., a VONSEAL® Liquid Tight Bag (Vonco Prods., Inc., Lake Villa, Ill.). In another embodiment, the component is a rigid container. In a specific embodiment, the rigid container is, as exemplified in FIG. 1, a screw-top jar or canister that is thick enough to withstand the changes in atmospheric pressure inherent in air transport. The canister may be constructed of any suitable material; in one embodiment, the canister is constructed of an opaque plastic such as high density polyethylene (HDPE). The component, e.g., canister or plastic shipping bag, should be large enough to contain the largest placenta. Thus, in various embodiments, the component is large enough to contain about 0.5, 0.6, 0.7, 0.8, 0.9, 1.0, 1.1, 1.2, 1.3, 1.4, 1.5, 1.6, 1.7, 1.8, 1.9 or 2.0 liters, or fractions thereof. In one embodiment, the component, e.g., canister or plastic shipping bag, is approximately 1.5 liters in volume. In another embodiment, the kit comprises a separate plastic bag 10, preferably sterile, in which the placenta is placed prior to placement of the placenta in the canister or plastic shipping bag. In one embodiment, the bag is sealable, and is labeled as containing biohazardous material. The bagged placenta is then placed into the component, e.g., canister or plastic shipping bag, for shipping.

The kits optionally further comprise a temperature controlling composition for maintaining and/or stabilizing the internal temperature of the insulating container during shipping. Maintaining the internal temperature of the kit at a temperature range around room temperature (e.g., around 23° C., for example, from about 15° C. to about 37° C.) during shipment of the collected cord blood and placenta helps maintaining the viability of the stem and progenitor cells in the cord blood, and helps maintain the viability of the stem and progenitor cells in the placenta. In embodiments in which the kit of the invention does not comprise a separate temperature controlling composition, the insulating container itself, optionally comprising a foam insert, provides sufficient temperature stabilization during shipping (e.g., for up to 24, 30, 36, 42 or up to 48 hours shipping time) to preserve the collected cord blood, placenta, and/or components thereof, e.g., cord blood and or placental stem and/or progenitor cells.

In various embodiments, the temperature-regulating or temperature controlling composition, e.g., a refrigerant, is capable of stabilizing temperature at or near room temperature (23° C.; e.g., 23° C.±3° C.), between room temperature and body temperature (approximately 37° C.), or between approximately 15° C. and approximately 30° C., or between 15° C. and approximately 37° C. The temperature controlling composition may be supplied in the kit in any acceptable configuration, such as a brick or, in one embodiment, a pack (e.g., gel pack). In one embodiment, the kit comprises a sufficient volume of temperature controlling composition to maintain a temperature of between about 15° C. and about 37° C., between about 15° C. and about 30° C., or between room temperature and body temperature (i.e., approximately 23° C. to approximately 37° C.) for at least a portion of the time during shipping. In one embodiment, the volume of temperature controlling composition in the kit is sufficient to maintain the kit's internal temperature in certain temperature ranges for more than 50%, 60%, 70%, 80%, 90%, or 95% of the time during shipping. In various embodiments, the kit contains 1, 2, 3, 4 or more temperature controlling composition (e.g., refrigerant) bricks or packs. In one embodiment, the kit contains 2 temperature controlling composition packs.

The temperature controlling composition may be selected for the particular temperature conditions expected during shipment. For example, for shipment in winter, the refrigerant may be one that resists drops in temperature more than spikes in temperature. Alternatively, for shipment in summer, or to or from areas that are generally hot, the refrigerant may be one that resists spikes in temperature better than drops in temperature. As used herein, "summer" may refer to the actual season, or any time when ambient temperatures are expected to exceed 23° C. at any time during shipment of the kit containing the collected cord blood and placenta, and "winter" may refer to the actual season, or any time when ambient temperatures are expected to fall below 23° C. at any time during shipment of the kit containing the collected cord blood and placenta. Alternatively, a temperature controlling composition may be used that resists spikes and drops in temperature approximately equally well. While any temperature controlling composition that improves the maintenance of the above-mentioned temperature ranges may be used in the present cord blood and placenta collection kit, where maintenance of a particular internal temperature is of paramount importance, suitable refrigerants may be those that maintain the internal temperature better, relative to other refrigerants. Examples of temperature controlling compositions include Koolit Phase Gel Packs from Cold Chain Technologies, Inc. (Holliston, Mass.), in particular, Koolit $PCM^{2626-X}$ for summer conditions, Koolit $PCM^{1616-b}$ for winter conditions, and Koolit PCM Phase Packs for all-weather temperature control. Also suitable is the Saf-T-Pak STP-317 15-30C refrigerant brick (Chesterton, UK) for all-weather temperature control.

Where the temperature controlling composition, e.g., refrigerant, is a brick or pack, the temperature controlling composition may be placed in any configuration suitable for maintaining the internal temperature. While the configuration of the temperature controlling composition is not critical as supplied to the user, the kit may instruct the user to place the temperature controlling composition on top of, under, or in one embodiment, both on top of and under the collected cord blood and placental container. Alternatively, in another embodiment, the kit may instruct the user to place the temperature controlling composition vertically on opposite sides of the interior of the cord blood and placenta collection kit, as exemplified by 2 in FIG. 1.

The cord blood and placenta collection kits of the invention may further comprise a device or composition that informs a user of the ambient temperature within the kit. Such a device may be, for example, a thermometer. The device may also be a composition that, for example, changes color, or turns a particular color, when a certain temperature or range of temperatures is reached. In one embodiment, said device or composition is, or can be, mounted on the outside of the collection kit, with a temperature sensor on the inside of the kit, so that the temperature of the kit's interior may be assessed without opening the kit.

The cord blood and placenta collection kits of the present invention further comprise components for collecting maternal blood. In one embodiment, such components are provided in the form of a kit, exemplified in FIG. 1 as 11. In one embodiment, the components for collecting maternal blood comprise one or more containers, such as vials, suitable for containing sufficient maternal blood for appropriate post-delivery blood analyses. The vials may contain a preservative, such as ethylenediaminetetraacetic acid (EDTA). The components also may comprise any other items that facilitate the collection of maternal blood, such as needles, alcohol swabs, and the like. In one embodiment, the components for maternal blood collection comprise a plurality of vials, e.g., four vials 12. In another embodiment, the components for maternal blood collection comprise two vials 12 containing EDTA and two vials 13 not containing EDTA. In another embodiment, the components for maternal blood collection comprise at least one needle suitable for blood collection. Any needle suitable for the collection of blood can be used, but preferred needles are from 20 gauge to 24 gauge, e.g., 22 gauge. In another embodiment, the components for maternal blood collection are provided in a container (e.g., a plastic tray as exemplified in FIG. 1 as 14) separate from the remaining contents of the cord blood and placenta collection kit. In another specific embodiment, the container is one or more plastic bags 22. In a specific embodiment, said container is a plastic tray storable in the lid of the insulating container of the cord blood and placenta collection kit.

The kits may additionally comprise instructions for the user. The instructions may be color-coded according to the particular procedure to be performed. In one embodiment, a first set of instructions, coded with a first color, serves to introduce the user to the cord blood and placental collection process, and instructs the user as to the forms to be filled out. In one embodiment, a second set of instructions, coded with a second color, instructs the user as to the timing and procedure for the collection of maternal blood. Finally, in one embodiment, a third set of instructions, coded with a third color, instructs the user with respect to the process of the collection of umbilical cord and placental blood, and of the placenta, and to the appropriate packing of the collected material into the kit and shipment of the kit to a cord blood or stem cell bank or registry. In one embodiment, the third set of instructions comprises instructions as to collection of cord blood prior to, or subsequent to, delivery of the placenta. In another embodiment, the third set of instructions comprises instructions for the collection of the placenta. In another specific embodiment, each of said sets of instructions is included in a single document, e.g., a tri-fold document. Because childbirth is a highly emotional and stressful time, the separation of the instructions by procedure, and color-coding of the separate instructions, represents an improvement in user convenience, as well as kit reliability and performance, over existing kits.

The kits provided by the present invention may additionally comprise a C-section adapter for placental blood and umbilical cord blood and placenta collection during C-section. The adapter may comprise a C-section adaptor, tubing sufficient in length to separate the collection bag(s) from the operating field; and/or a needle. Preferably, the C-section adaptor is a one-piece adaptor, and preferably comprises a needle guard. C-section adapters are available from, e.g., Centurion Scientific (Fenton, Mo.).

Finally, the kits may comprise other medical consumables that increase the convenience of the user during the cord blood and placenta collection procedure. For example, the kit may comprise one or more plastic bags for storing items; labels, for example, bar code labels for collection bags and the placenta canister; sterile gauze pads; chucks (i.e., blue absorbent pads); alcohol prep pads; medically-acceptable plastic or latex gloves; sterilization swabs (e.g., povidone-iodine swabs); and the like.

Thus, in one embodiment, the present invention provides a kit for the collection of placental and umbilical cord blood, and of a placenta, comprising (a) a container for the collection of said blood; (b) a container for the collection of said placenta; (c) materials sufficient for the collection of maternal blood; (d) instructions, wherein said instructions comprise a first set of instructions for the collection of maternal blood and a second set of instructions for the collection of umbilical cord and placental blood, wherein said first and second set of instructions are differently coded; and (e) an insulating container of sufficient capacity to contain items (a)-(d) prior to use, and items (a)-(c) after said collection of placental and umbilical cord blood, and of said placenta, wherein said kit does not comprise a temperature-controlling composition in addition to components (a)-(e). Optionally, the kit also comprises a temperature controlling composition. In a specific embodiment, said insulating container comprises an insert, e.g., a foam insert, comprising spaces suitable for holding a plurality, or all, of kit components, e.g., said container for the collection of said blood, container for the collection of said placenta, and/or materials sufficient for the collection of maternal blood.

In a specific embodiment, said container for the collection of blood is a blood bag. In a specific embodiment, the blood bag comprises a single bag. In another more specific embodiment, said blood bag comprises a plurality of bags. In a more specific embodiment, said blood bag comprises one large collection bag and three smaller satellite bags. The satellite bags allow for the aliquoting of small samples of the cord blood for analyses or diagnostics, without risk of contamination of the main store of blood.

In another specific embodiment, said materials for the collection of maternal blood comprises a plurality of vials and a needle suitable for the collection of blood. In specific embodiments, said needle is a 20 gauge, 21 gauge, 22 gauge, 23 gauge or 24 gauge needle. In a more specific embodiment, at least one of said plurality of vials comprises EDTA, and at least one of said plurality of vials does not contain EDTA. In another more specific embodiment, said materials for the collection of maternal blood are contained within a first container separate from the remaining contents of the kit. In a more specific embodiment, said first container fits into a hollow in the lid of said insulating container. In another specific embodiment, said materials for the collection of maternal blood comprise two vials containing EDTA and two vials not containing EDTA. In another more specific embodiment, said first container additionally comprises color-coded instructions for the use of said materials for the collection of maternal blood.

In another specific embodiment, said insulating container has a R value of between about 5 and about 8. In a more specific embodiment, said insulating container has an R value of about 6.5. In another more specific embodiment, the internal volume of said insulating container is between about 4 and about 8 liters. In a more specific embodiment, the volume of said insulating container is about 6 liters. In another specific embodiment, said insulating container comprises a lid having a central hollow suitable for receiving a first container that comprises a plurality of kit contents.

In another specific embodiment, said temperature controlling composition is a temperature controlling composition, e.g., a refrigerant, that resists temperature spikes. In another specific embodiment, said temperature controlling composition is a temperature controlling composition, e.g., a refrigerant, that resists temperature drops. In another specific embodiment, said temperature controlling composition is a temperature controlling composition that resists both temperature spikes and temperature drops. In another specific embodiment, said kit comprises a temperature controlling composition in brick or pack form. In another specific embodiment, said kit comprises a plurality of temperature controlling composition bricks or temperature controlling composition packs. In a more specific embodiment, said kit comprises two temperature controlling composition packs. In another more specific embodiment, said kit is designed to comprise two refrigerant packs in a vertical configuration on opposite sides of the interior of said insulating container. In another specific embodiment, said kit contains two temperature controlling composition packs, and instructs the user to place one pack above collected cord blood and one pack below collected cord blood prior to shipping. In another specific embodiment, said kit comprises two temperature controlling composition packs, and instructs the user to place at least one pack above collected cord blood and at least one pack below collected cord blood prior to shipping. In another specific embodiment, said kit comprises a sufficient volume of temperature controlling composition to maintain the interior of said insulating container between 15° C. and 37° C. during shipping of said kit to a cord blood bank or cord blood registry. In more specific embodiment, said kit comprises a sufficient volume of temperature controlling composition to maintain the interior of said insulating container between 15° C. and 37° C. during at least 12 hours of shipping of said kit to a cord blood bank or cord blood registry.

In a specific embodiment, the kit of the present invention comprises: (a) one or more single or individual blood bags; (b) a VONSEAL® Liquid Tight Bag, rated at 95 kPa, for the collection of a placenta; (c) materials sufficient for the collection of maternal blood, wherein said materials comprise one or more 22 gauge needles; (d) instructions, wherein said instructions comprise a first set of instructions for the collection of maternal blood and a second set of instructions for the collection of umbilical cord and placental blood, wherein said first and second set of instructions are differently coded; (e) a one-piece C-section adapter comprising a needle guard; (f) one or more CHLORAPREP® ONE-STEP FREPP applicator(s) and (e) an insulating container of sufficient capacity to contain items (a)-(f) prior to use, and items (a)-(c) after said collection of placental and umbilical cord blood, and of said placenta, wherein said insulating container is an attaché-style carrying case or box. The attaché-style carrying case or box can comprise a handle, e.g., a plastic handle, that enables the user to carry the kit as an attaché case or briefcase is carried (see, e.g., 24 in FIG. 2).

The present invention further provides a method of collecting placental blood and cord blood using the kit described herein. Typically, upon initiation of a relationship between a cord blood bank or registry and a user, the kit is sent to the user. In one embodiment, the kit, when opened, first presents a first set of instructions, as described above. The instructions may be color-coded. Later, the user takes the kit to the hospital, maternity ward, or other birthing place where medical personnel follow the second set of instructions, as described above, pertaining to collection of maternal blood. Collection of the maternal blood may take place either before or after delivery. Maternal blood collection may take place during delivery. Collection of placental and cord blood may, according to the third set of instructions, be obtained either before or after delivery of the placenta, and may be obtained in a normal childbirth, or in a Caesarean section. Collection of blood into the blood bag, and placenta into the canister, may be performed by medical personnel, though collection may be performed by the user. In one embodiment, the kit components are stabilized at room temperature (e.g., 23° C.±3° C.) immediately prior to collection. Upon collection, the blood bag, placenta canister, and maternal blood is placed in the kit's insulating container, and the insulating container sealed.

In one embodiment, the sealed insulating container is immediately placed in the hands of a delivery service or courier for delivery to a cord blood bank or registry, though delivery may be made within 24-72 hours.

Thus, in one embodiment, the present invention provides a method for the collection of umbilical cord blood and placental blood, and placenta, comprising using any of the cord blood and placenta collection kits described herein. In a specific embodiment, the kit comprises (a) a container for the collection of said blood; (b) a container for the collection of said placenta; (c) materials sufficient for the collection of maternal blood; (d) instructions, wherein said instructions comprise a first set of instructions for the collection of maternal blood and a second set of instructions for the collection of umbilical cord and placental blood, wherein said first and second set of instructions are differently coded; and (e) an insulating container of sufficient capacity to contain (1) items (a)-(d) prior to use, (2) items (a)-(c) after said collection of placental and umbilical cord blood, and (3) said placenta. Optionally, the kit comprises a temperature-controlling substance in one or more units (e.g., packs or bricks). In a more specific embodiment, the kit of the present invention comprises: (a) one or more single or individual blood bags; (b) a VONSEAL® Liquid Tight Bag, rated at 95 kPa, for the collection of a placenta; (c) materials sufficient for the collection of maternal blood, wherein said materials comprise one or more 22 gauge needles; (d) instructions, wherein said instructions comprise a first set of instructions for the collection of maternal blood and a second set of instructions for the collection of umbilical cord and placental blood, wherein said first and second set of instructions are differently coded; (e) a one-piece C-section adapter comprising a needle guard; (f) one or more CHLORAPREP® ONE-STEP FREPP applicator(s) and (e) an insulating container of sufficient capacity to contain items (a)-(f) prior to use, and items (a)-(c) after said collection of placental and umbilical cord blood, and of said placenta, wherein said insulating container is an attaché-style carrying case or box.

6. EXAMPLES

6.1 Cord Blood and Placenta Collection Kit

A kit was constructed that improves user convenience during placenta and cord blood collection during delivery, and improves the maintenance of the placenta and cord blood temperature during shipping to a blood and/or stem cell banking facility. The kit, called the Cord Blood Stem Cell Collection Kit, includes an insulating container in which blood and placenta collection components are stored, and a set of color-coded instructions. The kit is designed to be used by the layperson, with the assistance of medical personnel, and to be shipped both to the user prior to delivery, and to a blood bank post-collection, by a standard overnight delivery service.

The insulating container is made of Styrofoam, and has an R value is 6.5. The box has inside dimensions of 11×8½×7½ inches, which gives it an internal volume of approximately 11.5 liters. The lid of the box has a raised portion just inside the periphery of the lid, which fits into a channel or groove in the lid-receiving portion of the box. This raised portion/groove combination helps maintain the internal temperature of the box, as well as reducing the chance of leakage of the box' contents. As delivered to the user, the insulating container is surrounded by a shipping box made of corrugated cardboard. The shipping box includes a handle made from shaped folding portions of the top of the box.

As delivered to the user, the kit contains components that allow for the collection of the placenta and of the cord blood/ placental blood, and of the placenta itself. The components include:

(a) 1 umbilical cord blood collection bag (comprising a collection bag and three satellite bags);
(b) 1 clear plastic self-adhesive bag;
(c) 1 placenta carrier;
(d) 1 zip-lock placenta collection bag;
(e) 2 standard chucks (blue pads);
(f) 3 povidone-iodine swabs;
(g) 2 alcohol prep pads;
(h) 2 sterile gauze pads;
(i) 2 plastic umbilical cord clamps;
j) 1 set of non-sterile vinyl gloves;
(k) 1 slide clip; and
(l) 1 sterile C-section adaptor with extension tubing and 16-gauge needle.

The umbilical cord blood collection bag (a) comprises four chambers. The main chamber is large enough to hold all of the blood from the umbilical cord and placenta of a normal, non-twin birth. The collection bag additionally comprises three smaller chambers, approximately 10 cubic centimeters in volume, that are physically separate from the main chamber, but remain connected to the main chamber by plastic tubing. Blood collected into the main chamber may be aliquoted into the three smaller chambers during collection. After collection of blood, the blood collection bags are placed in a plastic self-adhesive bag (Biohazard) which is loosely placed inside the plastic cooler box.

The placenta carrier is a 1.5 liter plastic screw-top canister made of high-density polyethylene. The canister was obtained on a special-order basis from Exakt-Pak (Oklahoma City, Okla.). The canister has an O-ring that improves the seal between lid and canister body. The canister containing the bagged placenta is placed into a cardboard receiver in the bottom of the insulating container for shipping. The canister is sturdy enough to withstand the changes in pressure inherent in air transport.

The kit also includes a maternal blood collection kit, which contains:

a) two 7 mL lavender-top tubes containing 50 µl of an EDTA solution;
b) two 7 mL red-top tubes containing no solution;
c) 4 bar code labels for the lavender- and red-capped tubes;
d) 1 Vacutainer Safety-Lok Blood Collection Set (23 gauge) and yellow tube receiver; and
e) 2 sterile alcohol prep pads.

The maternal blood collection kit is contained in a plastic tray glued into a cavity in the underside of the insulating container lid. The components listed above are positioned in a block of shaped foam within the plastic tray. The plastic tray further includes a set of instructions for performing the timing of maternal blood collection and labeling of the tubes.

The kit further comprises two Saf-T-Pak STP-317 15-30C temperature controlling composition (refrigerant) bricks that help maintain the contents of the kit at a consistent temperature during shipping. The refrigerant bricks are designed to maintain temperature between 15-30° C. Each refrigerant brick is labeled with instructions not to freeze or microwave the block, and to precondition the blocks between 15-23° C. prior to shipping. The refrigerant bricks were obtained from Saf-T-Pak, Inc. As shipped to the user, the refrigerant bricks are positioned vertically against the two smaller inside faces of the insulating container.

The kit contains three color-coded sets of instructions. The first set, coded blue, provide users an overview of the cold/placental blood collection process, collection record forms, and reminders. The second set, coded green and labeled "Collection Step 1," instructs the user on the process of collecting maternal blood. The third set, coded red and labeled "Collection Step 2," instructs the user on umbilical cord/placental blood collection.

Finally, the kit contains the appropriate labels and bar codes for the maternal blood, placenta, and umbilical cord/placental blood, and a shipping label.

6.2 Effect of Configuration of Refrigerants During Shipping

A study was undertaken to determine the effect of different-configurations of kit contents and temperature controlling composition (refrigerant) packs on the internal temperature of an insulating shipping container, and on the temperature of various non-refrigerant kit contents, during a simulated 48 hours shipping time. The study used an insulating container having an R value of about 6.5 with an interior volume of about 6 liters. Kit contents tested included a maternal blood collection kit comprising four glass vials and a needle in a flat plastic tray, a plastic bag, and a blood bag. The plastic bag and blood bag were filled with material simulating a placenta and cord blood. For hot weather simulations, the refrigerant-containing kits contained Koolit $PCM^{2626-x}$ packs as the refrigerant. For cold weather simulations, the refrigerant-containing kits contained Koolit $PCM^{1616-x}$ packs. The following configurations of contents and refrigerant were tested:

I. Kit contents layered between two refrigerant packs on the bottom of the interior of the insulating container and two refrigerant packs on top of the kit contents;
II. Kit contents layered between two refrigerant packs on the bottom of the interior of the insulating container and four refrigerant packs on top of the kit contents;
III. Kit contents placed in insulating container with no refrigerants;
IV. Kit contents placed in the insulating container and covered with two refrigerant packs;
V. Maternal blood collection materials, in tray, taped to the underside of the insulating container lid; other kit contents placed in the insulating container and covered with two refrigerant packs;
VI. Maternal blood collection materials, in tray, taped to the underside of the insulating container lid; two refrigerant packs are placed on the bottom of the interior of the insulating container, other kit contents are placed on these two refrigerant packs, and covered with two additional refrigerant packs;
VII. Maternal blood collection materials, in tray, placed in a cavity formed in the underside of the insulating container lid; two refrigerant packs placed on the bottom of the interior of the insulating container, other kit contents placed on these two refrigerant packs, and covered with two additional refrigerant packs; and
VIII. Maternal blood collection materials, in tray, placed in a cavity formed in the underside of the insulating container lid; other kit contents placed in the insulating container and covered with two refrigerant packs.

For each of the above configurations, thermocouples were attached to the tray containing the maternal blood collection components, the bag containing the simulated placenta, the bag containing the simulated blood; and one was set to record the ambient internal temperature of the insulating container. In each case, the lid of the insulating container was taped shut and the temperature, as detected by the thermocouples, recorded over 48 hours. For each of the configurations above, the kit contents were stabilized at 22° C.±3° C. prior to taping the lid shut.

During the 48 hours of the studies, temperature spikes were used to simulate varying temperature conditions during shipping. In one set of experiments simulating shipping during summer or hot-weather conditions using the above configurations, the temperature exterior to the sealed kit was maintained at 22° C. for seven hours; brought to 44° C. over the course of two hours; held at 44° C. for two hours; brought to 30° C. over the course of two hours; maintained at 30° C. for 12 hours; brought to 44° C. over the course of two hours; held at 44° C. for two hours; brought to 30° C. over the course of two hours; and maintained at 30° C. for the remainder of the 48 hours of the experiment.

In another set of experiments simulating shipping during winter or cold-weather conditions using the above configurations, the temperature exterior to the sealed kit was maintained at 18° C. for six hours; brought to −20° C. over the course of two hours; maintained at −20° C. for two hours; brought to 10° C. over two hours; held at 10° C. for twelve hours; brought to −20° C. over the course of two hours; maintained at −20° C. for two hours; brought to 10° C. over two hours; and held at 10° C. for the remainder of the 48 hours.

For both sets of simulations, configurations I and II performed the best. In simulated hot weather shipping conditions, internal temperatures recorded by any thermocouple never rose above 27° C. Similarly, in simulated cold weather shipping conditions, internal temperatures recorded by any thermocouple never fell below 13° C. Other configurations allowed for more variation in internal or kit component temperature, but, with the exception of configuration II, such temperatures never exceeded 34° C. or fell below 4° C.

6.3 Effect of Different Refrigerants on Internal Temperature

The objective of this test is to perform thermal qualification testing for cord blood stem cell collection kit's shipping container. A total of six EPS shipping containers (TL-1187) were tested. The product load was the same for all six containers. Three containers were packed each with 2-Phase Pack refrigerants and the other three containers were packed each with Two Koolit $PCM^{1116-b}$ refrigerants from Cold Chain Technologies. Blood and placenta containers were filled with a phantom gel to simulate collected tissue. Shippers were tested for 48 hours utilizing ISTA 7D external ambient guideline profile.

Test Results Overview: Test results indicated that the EPS shipping containers packed with the Koolit $PCM^{1616-b}$ refrigerants provided better thermal protection to the product load based on the recorded product temperatures during the 48-hour test. The results are recapped below.

TABLE 1

Results of simulated cold-weather challenge using different refrigerants. Recorded Product Temperatures under Winter Challenge

| Test # 1796 | Refrigerant Used | Lowest Product Temperature (Centigrade) | Average Product Temperature (Centigrade) |
|---|---|---|---|
| 1b | Koolit PCM | 5.9 | 14.5 |
| 2a | Koolit PCM | 6.1 | 14.5 |

TABLE 1-continued

Results of simulated cold-weather challenge using different refrigerants.
Recorded Product Temperatures under Winter Challenge

| Test # 1796 | Refrigerant Used | Lowest Product Temperature (Centigrade) | Average Product Temperature (Centigrade) |
|---|---|---|---|
| 2b | Koolit PCM | 6.0 | 14.6 |
| 1a | Phase Pack | −1.8 | 10.6 |
| 1c | Phase Pack | −1.0 | 10.6 |
| 2c | Phase Pack | −1.8 | 10.7 |

1a and 1b: 75% phantom gel.
2a and 1c: 80% phantom gel.
2b and 2c: 85% phantom gel.

6.4 Improved Cord Blood and Collection Kit

A kit was constructed that improves user convenience during placenta and cord blood collection during delivery, and improves the maintenance of the placenta and cord blood temperature during shipping to a blood and/or stem cell banking facility. The kit includes an insulating container in which blood and placenta collection components are stored, and a set of color-coded instructions. The kit does not include, and does not require, a temperature controlling composition. The kit is designed to be used by the layperson, with the assistance of medical personnel, and to be shipped both to the user prior to delivery, and to a blood bank post-collection, by a standard overnight delivery service.

The kit comprises an insulating container that both comprises the kit contents and is used to ship collected materials to be processed. The insulating container comprises a corrugated cardboard box, the interior surface of which is lined with STYROFOAM™ that is about 0.75 inches thick. The STYROFOAM™ covers substantially all of the interior surface of the cardboard box. The insulating container comprises a foam insert, the exterior of which abuts the interior face of the STYROFOAM™. The foam insert has three spaces for receiving and storing collection components; a large space holds the umbilical cord blood and placenta collection materials, while two smaller spaces hold the maternal blood-draw tubes and remaining maternal blood-draw materials, respectively. One face of the insulating container comprises a plastic handle to facilitate carriage of the container, e.g., by a user of the kit.

As delivered to the user, the kit contains components that allow for the collection of cord blood/placental blood, placenta, and maternal blood. The components include:

1. Umbilical cord blood collection materials, including:
   (a) 1 color-coded umbilical cord blood collection bag (single bag) comprising citrate phosphate dextrose solution, with bar coded-label (Baxter Healthcare Corporation, Deerfield, Ill.);
   (b) 1 clear plastic self-adhesive bag for transport of the cord blood in the collection bag;
   (c) 2 plastic umbilical cord clamps;
   (d) 2 applicators for delivery of an antibacterial, e.g., a solution of chlorhexidine gluconate 2% (w/v), isopropyl alcohol 70% (v/v);
   (e) 1 gauze sponge;
   (f) 1 sterile C-section adaptor with extension tubing and 16-gauge needle (e.g., from Centurion Scientific, Inc., Fenton, Ill.);
   (g) 1 needle guard; and
   (h) Pinch clamp for stripping blood bag tubing;

2. Placenta collection materials, including:
   (a) 1 clear plastic self-adhesive specimen transport bag for transport of the placenta, rated at 95 kPa (e.g., VON-SEAL® Liquid Tight Bag, Vonco Prods., Inc.; and
   (b) 1 zip-top bag to contain the placenta; and 3. Maternal blood draw materials, including:
   (a) 1 22 gauge needle;
   (b) 1 VACUTAINER™ one-use holder, or the like;
   (c) 2 sterile alcohol prep pads;
   (d) 1 zip-top bag;
   (e) 4 blood collection tubes (about 6 mL); and
   (e) identification bar code labels.

The kit contains three color-coded sets of instructions. The first set, coded yellow and labeled "Cord Blood Collection Procedure", provides users an overview of, and steps for, the cord/placental blood collection process. The second set, coded green and labeled "Maternal Blood-Draw Procedure", instructs the user on the process of collecting maternal blood. The third set, coded red and labeled "Placenta Collection Procedure", instructs the user on collection of the placenta.

Finally, the kit contains the appropriate labels and bar codes for the maternal blood, placenta, and umbilical cord/placental blood, and a shipping label.

The kit comprises no temperature-controlling composition; the insulating container is sufficient to maintain the temperature of the collected materials during routine shipping for 24-72 hours, typically 48 hours.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A kit comprising (a) a container for the collection of placental or umbilical cord blood; (b) a container for the collection of said placenta; (c) materials sufficient for the collection of maternal blood; (d) instructions, wherein said instructions comprise a first set of instructions for the collection of maternal blood, a second set of instructions for the collection of umbilical cord and placental blood, and a third set of instructions for collection of said placenta, wherein said first, second and third sets of instructions are differently coded; and (e) an insulating container of sufficient capacity to contain (1) items (a)-(d) prior to use, (2) items (a)-(c) after said collection of placental and umbilical cord blood, and (3) said placenta, wherein said kit does not comprise a temperature controlling composition in addition to components (a)-(e).

2. The kit of claim 1, comprising a foam insert within said insulating container, said foam insert comprising space for the storage of kit components and collected placenta and umbilical cord blood.

3. The kit of claim 2, wherein said foam insert comprises a first space sufficiently large to hold said container for the collection of said placenta and a placenta, and said container for the collection of placental or umbilical cord blood, and said placental or umbilical cord blood; a second space sufficiently large to contain a plurality of maternal blood collection vials; and a third space sufficiently large to comprise a blood collection needle and alcohol swabs.

4. The kit of claim 1, wherein said container for the collection of blood is a blood bag.

5. The kit of claim 1, wherein said container for the collection of said placenta is a sealable plastic bag rated to withstand 95 kPa internal pressure.

6. The kit of claim 1, wherein said materials for the collection of maternal blood comprise a plurality of vials and a needle suitable for the collection of blood.

7. The kit of claim 1, wherein said materials for the collection of maternal blood comprise one or more 22 gauge needles.

8. The kit of claim 7, wherein at least one of said plurality of vials comprises EDTA, and at least one of said plurality of vials does not contain EDTA.

9. The kit of claim 1, wherein at least some of said materials for the collection of maternal blood are contained within a first container separate from the remaining contents of the kit.

10. The kit of claim 9, wherein said first container additionally comprises color-coded instructions for the use of said materials for the collection of maternal blood.

11. The kit of claim 1, wherein said insulating container is an attaché-style carrying case or box.

12. A method for the collection of umbilical cord blood or placental blood, and of a placenta, comprising using a kit which comprises (a) a container for the collection of said placental blood or umbilical cord blood; (b) a container for the collection of said placenta; (c) materials sufficient for the collection of maternal blood; (d) instructions, wherein said instructions comprise a first set of instructions for the collection of maternal blood and a second set of instructions for the collection of umbilical cord and placental blood, wherein said first and second set of instructions are differently coded; and (e) an insulating container of sufficient capacity to contain (1) items (a)-(d) prior to use, (2) items (a)-(c) after said collection of said placental blood or umbilical cord blood, and (3) said placenta, wherein said kit does not comprise a temperature-controlling composition.

13. The method of claim 12, comprising a foam insert within said insulating container, said foam insert comprising space for the storage of kit components and collected placenta and umbilical cord blood.

14. The method of claim 13, wherein said foam insert comprises a first space sufficiently large to hold said container for the collection of said placenta and a placenta, and said container for the collection of placental or umbilical cord blood, and said placental or umbilical cord blood; a second space sufficiently large to contain a plurality of maternal blood collection vials; and a third space sufficiently large to comprise a blood collection needle and alcohol swabs.

15. The method of claim 12, wherein said container for the collection of blood is a blood bag.

16. The method of claim 12, wherein said container for the collection of said placenta is a sealable plastic bag rated to withstand 95 kPa internal pressure.

17. The method of claim 12, wherein said materials for the collection of maternal blood comprise a plurality of vials and a needle suitable for the collection of blood.

18. The method of claim 12, wherein said materials for the collection of maternal blood comprise one or more 22 gauge needles.

19. The kit of claim 18, wherein at least one of said plurality of vials comprises EDTA, and at least one of said plurality of vials does not contain EDTA.

20. The method of claim 12, wherein at least some of said materials for the collection of maternal blood are contained within a first container separate from the remaining contents of the kit.

21. The method of claim 20, wherein said first container additionally comprises color-coded instructions for the use of said materials for the collection of maternal blood.

22. The method of claim 12, wherein said insulating container is an attaché-style carrying case or box.

* * * * *